United States Patent [19]

Skovajsa

[11] 4,232,678

[45] Nov. 11, 1980

[54] DEVICE FOR THE LOCAL TREATMENT OF A PATIENT, AND MORE PARTICULARLY APPLICABLE IN ACUPUNCTURE AND AURICULOTHERAPHY

[76] Inventor: Joseph Skovajsa, 19, Avenue Vauquelin, 93 Coubron, France

[21] Appl. No.: 905,938

[22] Filed: May 15, 1978

[30] Foreign Application Priority Data

May 16, 1977 [FR] France .................... 77 14907
Aug. 1, 1977 [FR] France .................... 77 23616

[51] Int. Cl.³ .............................................. A61N 5/00
[52] U.S. Cl. .................................................. 128/395
[58] Field of Search ............................ 128/395–398, 128/303.1, 2.1 C, 419 R, 362, 421, 422, 423 R, 735, 907

[56] References Cited

U.S. PATENT DOCUMENTS

| | | | |
|---|---|---|---|
| 3,315,680 | 4/1967 | Silbertrust et al. ................ | 128/395 |
| 3,773,049 | 11/1973 | Rabichev et al. ................... | 128/362 |
| 3,818,914 | 6/1974 | Bender .............................. | 128/396 |
| 3,900,034 | 8/1975 | Katz et al. ........................ | 128/395 |
| 4,052,978 | 10/1977 | Eugenio ........................... | 128/2.1 C X |
| 4,074,110 | 2/1978 | Slaughter ........................ | 128/303.1 X |
| 4,093,975 | 6/1978 | Roberts ........................... | 128/419 R X |
| 4,112,923 | 9/1978 | Tomecek ......................... | 128/419 R X |

FOREIGN PATENT DOCUMENTS 2258872 8/1975 France .................................... 128/395

Primary Examiner—Lee S. Cohen
Attorney, Agent, or Firm—Thomas J. Greer, Jr.

[57] ABSTRACT

A device for the local treatment of a patient by acupuncture or auriculotherapy. Instead of needles, a treatment head is approached the body of the patient. It includes an infra-red laser diode being excitable recurrently and in a controlled manner. The recurrence frequency is selectable among a plurality of discrete frequencies, each of which may be finely adjusted.

3 Claims, 6 Drawing Figures

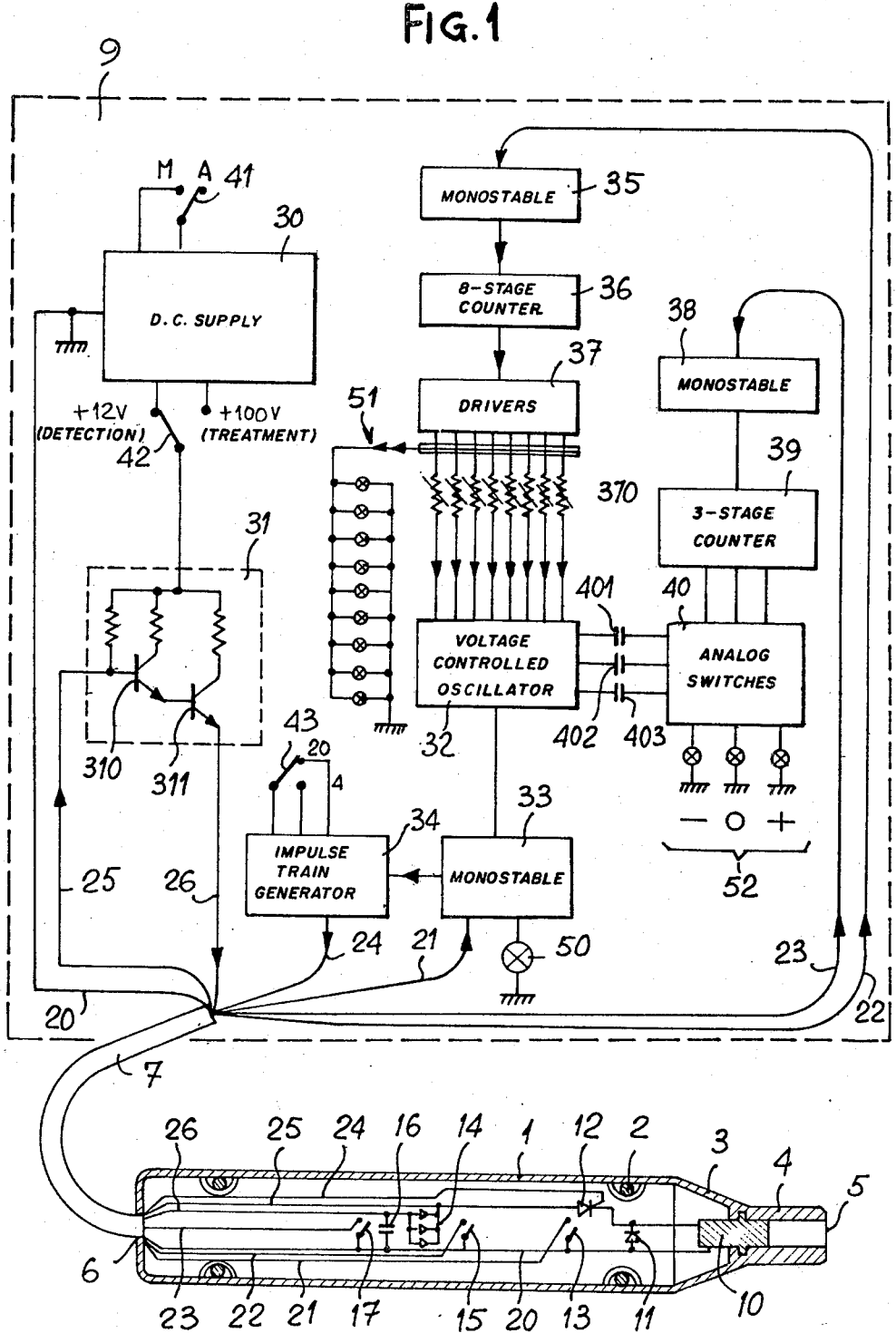

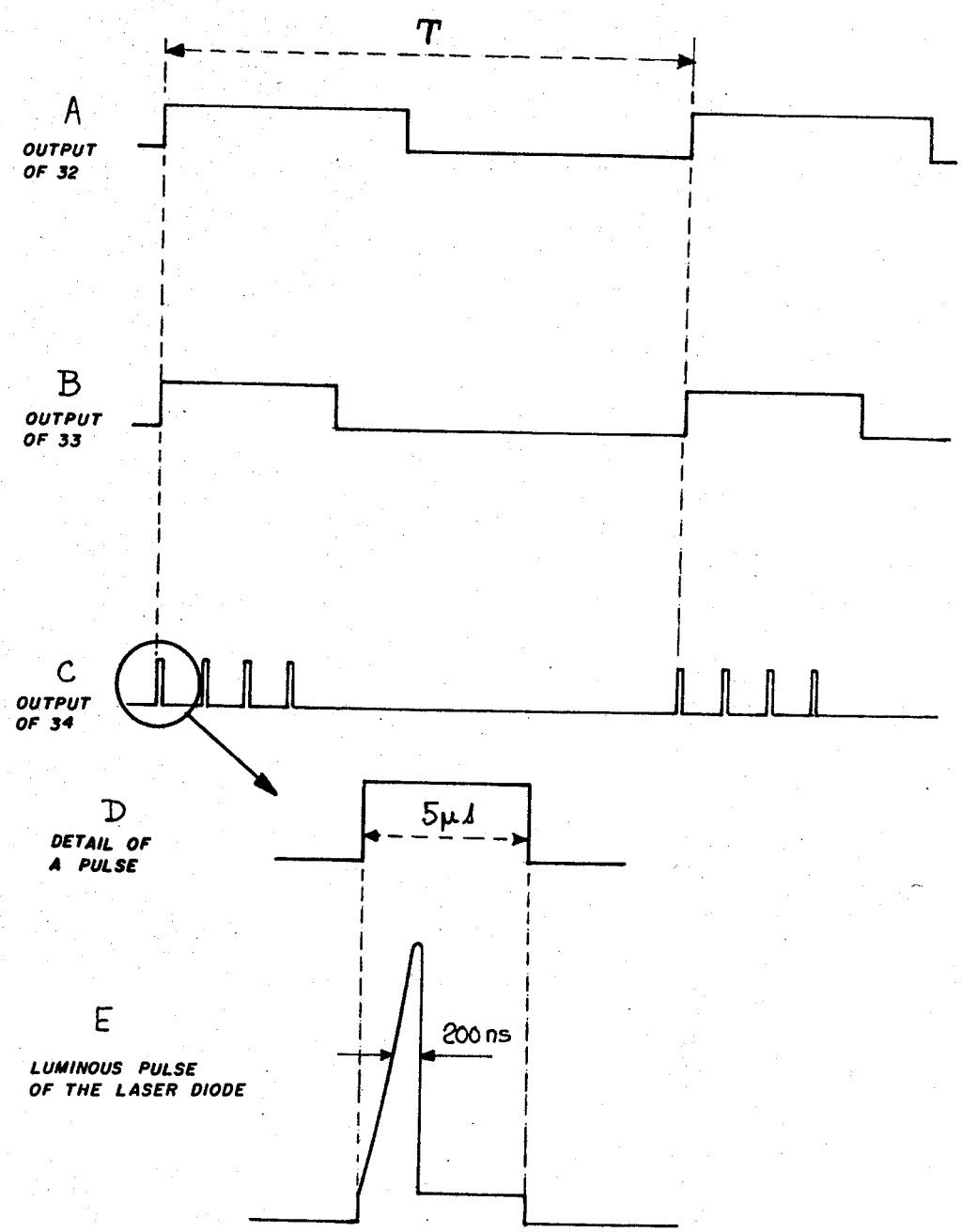

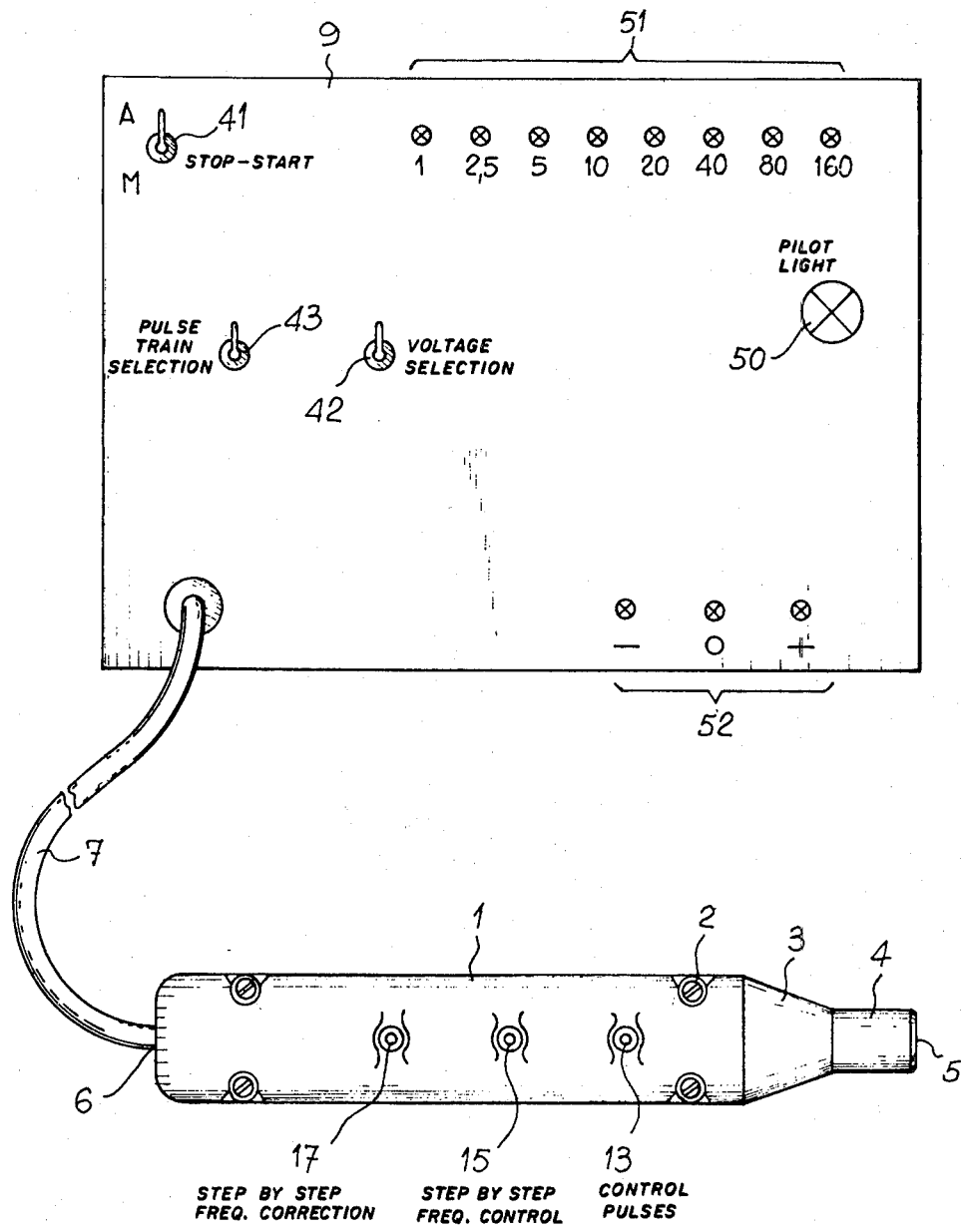

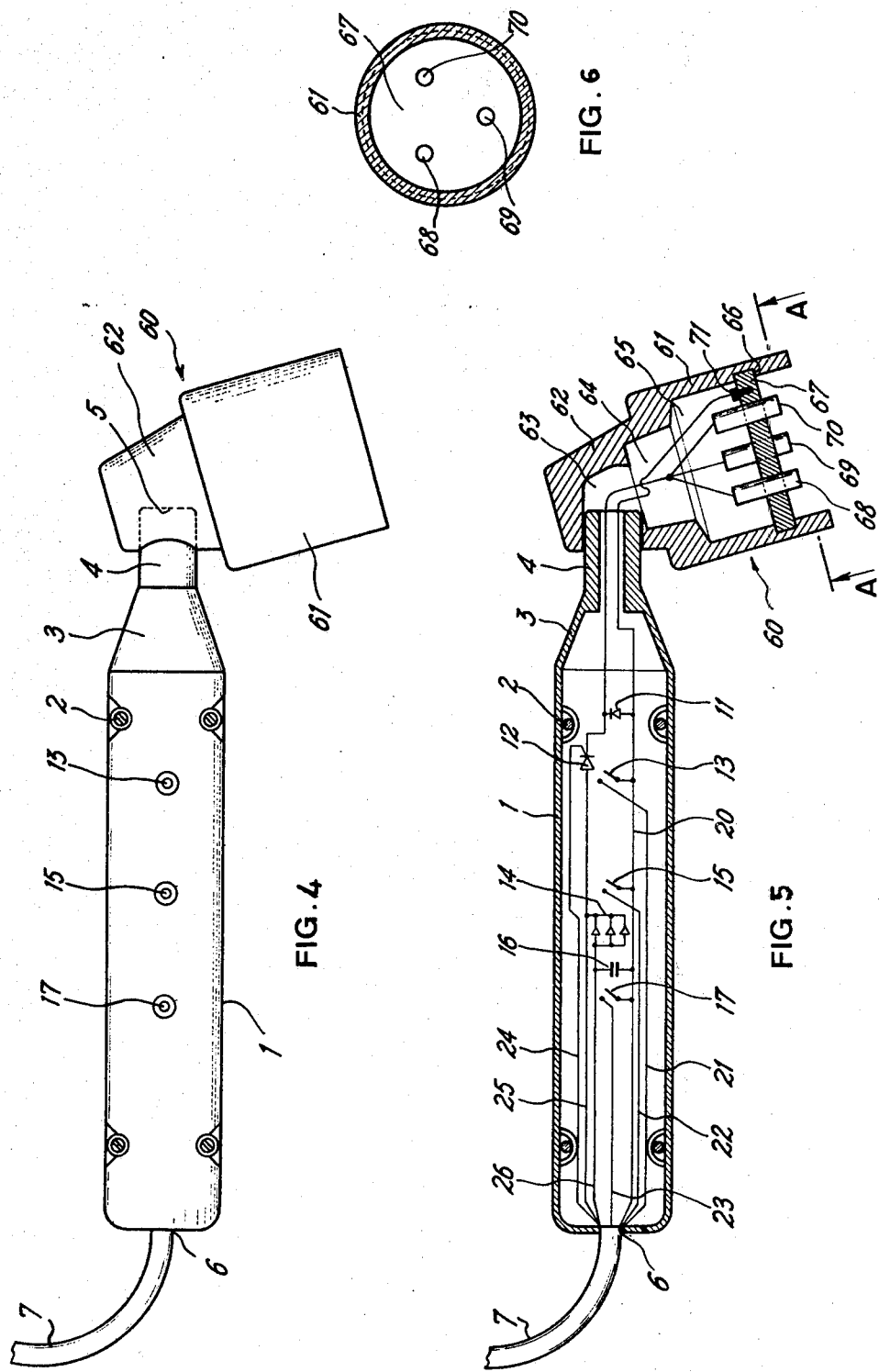

DEVICE FOR THE LOCAL TREATMENT OF A PATIENT, AND MORE PARTICULARLY APPLICABLE IN ACUPUNCTURE AND AURICULOTHERAPHY

The present invention relates to a device for the local treatment of a patient, and is more particularly applicable in acupuncture and auriculotherapy.

Conventional acupuncture is known to use needles implanted at selected spots in the patient's body in order to treat and/or cure certain types of disorders. Auriculotherapy is a variant of this, in which the needles are implanted on the ear, it being observed that there is a biunivocal correspondence between the points of the ear and the internal organs of the patient's body.

The present invention offers a novel treating device of this type, in which the implantation of a needle is replaced by an application of localised energy. To this end, the device generally comprises a treatment head provided with a laser diode, and connected to a supply unit.

More precisely, the treatment head is in the form of an elongated body terminating in a treatment orifice and comprises a device with laser diode, of which the illuminant end is mounted in operational relationship with the treatment orifice. The supply unit comprises means for supplying the laser diode recurrently and in controlled manner.

The laser diode preferably emits at a wavelength in the infrared range, advantageously around 9000 Angström.

It is sometimes preferable, for certain applications, to use a plurality of laser diodes. In this case, an end piece is added to the treatment head, which end piece is mounted on the treatment orifice side. This end piece itself supports a plurality of laser diodes. The wires supplying same pass through the end orifice of the treatment head. In order suitably to supply a plurality of laser diodes, it suffices simply to increase the capacity of the capacitor which will discharge therethrough in controlled manner by the thyristor.

The invention will be more readily understood on reading the following description with reference to the accompanying drawings, in which:

FIG. 1 illustrates a schematic view, in section, of the treatment head, with circuits which it contains, as well as the electrical diagram of the supply unit of this treatment head;

FIG. 2 is a series of time vs. voltage diagrams illustrating the functioning of the device of FIG. 1; and FIG. 3 illustrates the outer appearance of the treatment head with its three control switches, as well as the front face of the supply unit.

FIG. 4 illustrates an outside view of a treatment head provided with an end piece with multiple laser diodes.

FIG. 5 illustrates a view in section of the head of FIG. 4.

FIG. 6 is a view along A—A of FIG. 5.

Referring now to the drawings, FIGS. 1 to 3 show the treatment head generally referenced 1. It is constituted by a body of generally cylindrical shape, terminating in a truncated portion 3 then finally in a short cylindrical portion 4 of small diameter, at the end of which is made the treatment orifice 5. At the other end is provided another axial orifice 6 for the passage of a multiple wire 7 for connection with the treatment assembly, which for its part is designated by general reference 9.

The treatment head 1 is constituted by two halves, the upper half being removed in FIG. 1. These two halves are connected by screws 2.

FIG. 1 shows a laser diode 10, which is housed in the truncated portion 3 of the treatment head 1. The illuminant end of the laser diode 10 is mounted in operational relationship with the treatment orifice 5.

The laser diode emits in the infrared range, preferably at a wave length of 9000 Angström.

A protecting diode 11 is mounted in inverse manner at the terminals of the laser diode 10. One of the terminals of this assembly is connected to the common conductor 20, whilst the other terminal is connected to the cathode of a thyristor 12. The gate of this thyristor 12 is directly connected to a conductor 24 terminating at connection 7. The anode of the thyristor 12 is connected in the first place to an assembly of three diodes 14 mounted in parallel, on the cathode side of these diodes. The anodes of these same diodes are connected together and to a terminal of a capacitor 16, as well as to a conductor 26 terminating at the connection 7. The other armature of the capacitor 16 is connected to the common conductor 20. Finally, the anode of the thyristor 12 is directly connected to a conductor 25 which also goes towards the connection 7.

This assembly forms a laser diode device. The capacitor 16 is normally charged at a positive voltage in the manner defined hereinafter. Via the diodes 14, it may transmit this voltage to the anode of the thyristor 12. When its gate is actuated, the thyristor switches on the laser diode 10, this producing a sharp discharge of the capacitor 16, and the appearance of a luminous laser plus which is transmitted through the orifice 5. FIGS. $2^D$ and $2^E$ respectively illustrate a pulse controlling the gate of the thyristor 12 and the luminous response of the laser diode to this pulse. It will be noted that for a pulse controlling the gate which lasts 5 micro-seconds, the duration of the laser pulse at its half-amplitude is about 200 nano seconds.

According to a particularly advantageous feature of the preferred embodiment of the invention, the treatment head 1 comprises three push-button switches 13, 15 and 17 respectively in FIGS. 1 and 3. As will be seen hereinafter, the push button 13 allows the application of control pulses in pre-established manner to the gate of the thyristor 12, and the subsequent actuation of the laser diode 10. The push button 15 effects a step by step frequency control among a set of 8 preestablished values. Push button 17 effects a step by step frequency correction control, the frequency being exactly the pre-established value, a value higher by 20%, or a value lower by 20%. For its part, the supply unit firstly comprises a D.C. supply unit 30 connected for example to the A.C. mains. This unit is provided with a general stop-start switch 41. Its ground is connected to the common conductor 20 which has already been mentioned of the treatment head 1, and of course to the ground of all the other elements of the supply unit. In addition to the supply of these same elements, the D.C. supply unit 30 furnishes on the one hand a voltage of +12 volts and on the other hand a voltage of +100 volts. A switch 42 enables one of these two voltages to be chosen, in order to apply it to a constant current generator circuit 31. The latter is made in known manner from two transistors 310 and 311 arranged as double common collector. The functioning is as follows: when the thyristor 12 of the treatment head is conducting, its anode is at a relatively low potential, and it then blocks the transistor 310 and consequently the transistor 311. In all other cases, the anode voltage of the thyristor 12 is imposed only by the resistor connecting the base of the transistor 310 to the D.C. supply. The transistors 310 and 311 are then conducting in order to charge capacitor 16 according to a substantially constant current. In summary, in the normal state, the capacitor 16 is charged permanently. This discharge is interrupted only at those moments when the thyristor is conducting, this being controlled by its gate as will now be seen.

The conductor 24 connects this gate of the thyristor 12 to a pulse train generator 34. Said latter is under the action of a monostable 33, and for each pulse of the monostable 33, it supplies a pulse train which comprises either 4 pulses or 20 pulses, for example in controlled manner by a switch 43. It is this monostable 33 which is under the action of the push button 13 controlling the light beam. The monostable 33 is therefore normally inhibited. When the push button 13 is actuated, the monostable 33 is then free to function, acting on the pulse train generator 34 and lighting a "laser function" pilot lamp 50.

Furthermore the monostable 33 is itself under the action of an oscillator 32, which constitutes the heart of the supply unit. This oscillator 32 is of the type controlled by a voltage, and possesses in this preferred embodiment three different tuning capacitors 401, 402 and 403.

Its control by a voltage will firstly be described. This voltage is controlled by the push button 15 which actuates, via the conductor 22, a monostable 35. Any pressure on the push button 15 produces an output pulse of the monostable 35, this having for its effect to increment a counter with 8 stages, mounted as a ring, designated by reference 36. By actuating the push button, each of the eight stages of the counter may therefore be successively actuated. These eight stages are respectively coupled to driver transistors 37, which respectively control associated adjustable resistors referenced 370. Thus, there corresponds to each position of the counter 36 the switching on of one of the resistors 370, this giving a particular control voltage for the oscillator, and consequently defining a frequency therefor. The outputs of the drivers, 37 also control a set of pilot lamps 51, which indicate which of the frequencies is presently controlled.

The last push button of the treatment head 1 acts for its part on another monostable 38 coupled to another counter 39 with three stages mounted as a ring. The three stages of the counter are respectively coupled to three analog switches 40, which selectively switch on one of the capacitors 401, 402 and 403 respectively, whilst at the same time lighting one of the pilot lamps 52.

Finally, it is therefore one of the resistors 370 which defines the basic frequency at which the oscillator 32 will function. And it is the capacitor 401 to 403 which is switched on which will define the precise value of this frequency, namely whether the frequency is taken exactly, increased by 20% or reduced by 20%.

The output of the oscillator 32 is in rectangular form and possesses the final rate shown in FIG. 2A. Under these conditions, the frequency of the oscillator 32 is in fact a repetition rate, and it is the inverse of the period T of the output signal. This period T is found in FIG. 2, and it is the time gap between the beginnings of two consecutive rectangular gates. FIG. 2B indicates the output of the monostable 33. This output is constituted by gates of same period T as those of the oscillator 32, but of a slightly shorter duration. As has already been noted this output of the monostable 33 exists only when the push button 13 for controlling the beam is actuated. Then, for each gate of the monostable 33, the pulse generator 34 furnishes 4 or 20 pulses lasting about 5 micro-seconds, according to the position of the switch 43. As indicated in FIG. 2D and 2E, the production of a luminous pulse by the laser diode 10 corresponds to each of these pulses.

The application of the device according to the invention may now be briefly described with reference to FIG. 3.

The device is switched on by the general switch 41. Switch 43 is positioned according to whether it is question of a stimulation or dispersion, the first corresponding to 20 pulses per train and the second to 4 pulses. These concepts of stimulation and dispersion are well known in acupuncture and auriculotherapy. In a first phase, a switch 42 is placed in position of detection to apply a low voltage of 12 volts to the laser diode. This will furnish only a very weak illuminating pulse, and allows the detection of the points of acupuncture. This detection having been effected, the switch 42 will then be placed in position of treatment, for the application of the total energy to the points of acupuncture or auriculatherapy which will have been determined.

In the preferred embodiment, the basic frequencies are as follows: 1 Hz, 2.5 Hz, 5 Hz, 10 Hz, 20 Hz, 40 Hz, 80 Hz and 160 hz. It has been observed that these frequencies correspond respectively to particular living tissues, precisely associated. The choice of frequency is made in step by step control under the action of the push button 15. It has also been observed that certain disorders required a slightly different frequency. A correction of +20% or −20% is possible under the action of the push button 17. The frequency selected and its correction, if need be, are displayed by the pilot lamps 51 and 52.

It then remains to actuate the push button 13 for controlling the beam, this bringing about the production of light pulses and the simultaneous illumination of the "beam" pilot lamp 50.

As indicated hereinabove, after using the device for diagnosis of the points of acupuncture or auriculotherapy, it may be used for treatment at the same points, after the switch 42 has been reversed.

The apparatus according to the invention advantageously replaces the treatment which is conventionally carried out in acupuncture and auriculotherapy. Of course, the invention is not limited by the features of the preferred embodiment which have been given hereinabove.

It suffices that the supply unit comprises means for supplying the device with laser diode recurrently and in controlled manner. The laser diode essentially comprises the laser diode, a thyristor and a capacitor. For sufficiently high supply voltages, a laser triggering may be obtained. The time constant of the circuit is chosen for a brief laser triggering to be produced after the charging of the capacitor with a sufficiently high D.C. voltage, and after the triggering of the control electrode of the thyristor.

The supply unit further comprises a first generator supplying a basic recurrence signal at chosen frequency. In the embodiment described, this first generator articulates about the oscillator 32. It also comprises a second generator controlled by this recurrence frequency and producing for each basic recurrence signal a pulse train. These pulse trains are the ones which are applied in controlled manner to the gate of the thyristor.

Of course, variants of the device of the invention may easily be found, both from the electrical and mechanical points of view. For example, for certain applications, it possibly surffices to couple a short optical fibre to the treatment orifice 5. This is the case for dental treatment in particular.

In a particular embodiment, the treatment head comprises a plurality of laser diodes (the capacity of the capacitor 16 being suitably increased to be able to supply all the diodes of the head). This embodiment is described in FIGS. 4 to 6.

FIGS. 4 and 5 show that the treatment head is provided with an end piece 60 which comprises a wide cylindrical portion 61, extended by a truncated portion 62. In this truncated portion 62 is made an inner cavity 63 which is open on one side, to receive the cylindrical end 4 of the treatment head tightly. This inner cavity 63 continues in a wider inner cavity 64, then in a cylindrical inner cavity 65, located at the level of the cylindrical portion 61 of the end piece. The walls of the cavity 65 include a notch 66 in which is housed a conducting disc 67. This disc firstly comprises a stud 71. It also comprises three bores, in which are mounted three laser diodes 68, 69 and 70. The laser diodes are mounted so that one of their output connections is in contact with the conducting disc 67, and consequently with the conducting stud 71.

FIG. 6 shows more clearly that the three diodes 68, 69 and 70 are mounted in a triangle, and are substantially symmetrical with respect to the centre of the disc 67.

From the electrical point of view, the ground connection of the laser diodes is therefore connected to the stud 71 which is itself connected to the anode of the diode 11 located in the treatment head. The cathode of this diode 11 is connected to each of the other output terminals of the laser diodes 68, 69 and 70.

In the embodiment of FIGS. 1 to 3, it has been indicated that the supply unit acts on the one hand for charging the capacitor 16 and on the other hand for applying control pulse to the thyristor 12. In the case of FIGS. 4 to 6, upon each control pulse, the three laser diodes will be lit simultaneously, the increased capacity of the capacitor 16 allowing suitable functioning.

Whilst the treatment head of FIGS. 1 to 3 is very suitable for point-like treatments, the treatment head of FIGS. 4 to 6 is particularly applied to the case of a zone treatment being desirable. This is particularly the case with strains and dislocations, especially of the ankles and knees. It is also applicable for skin and sub-cutaneous disorders, injuries or burns. The device with multiple diodes has also proved excellent for the treatment of osseous calluses.

What is claimed is:

1. A device for point-treatment of a patient, comprising a treatment head, a power supply unit, and a flexible connection therebetween, at least one laser diode carried by said treatment head, said treatment head comprising a body of generally cylindrical form, which terminates in a truncated portion, said truncated portion carrying a short cylindrical portion of smaller diameter than the diameter of said cylindrical body, said short cylindrical portion having an interior surface for defining a treatment orifice for selectively receiving said laser diode and an exterior surface for defining a mounting surface for mounting a separate end piece for selectively receiving said laser diode, and laser control energizing means located within said treatment head for controlling the laser diode, so that said diode emits laser pulses of light, said supply unit including means for applying trains of electric pulses to said laser control energizing means recurrently and in a controlled manner, said energizing means comprising a capacitor and a thyristor arranged in series circuit relationship with said laser diode, said supply unit including means connected across the capacitor and capable of charging the same, while electric pulses are applied to the control gate of said thyristor, the power supply unit including means for furnishing the laser diode with two different D.C. voltages, the lower voltage serving for detection purposes without considerable laser stimulation, the stronger voltage serving for the treatment with laser pulses, the power supply unit including means for switching a frequency parameter of said electric pulses, cyclically among a predetermined plurality of frequency values, and wherein the treatment head carries a first manual switch means for controlling energization of said laser diode, said treatment head also carrying a second manual switch means for controlling said cyclic switching of the frequency parameter, said means for switching a frequency parameter including a first generator in the supply unit, the basic recurrence frequency of the first generator being switchable among a plurality of selected frequencies, including means for adjusting the frequency parameter, step by step correction control means in said supply unit for effecting said adjustment of the frequency parameter, and wherein said treatment head includes a third manual switch means for actuating said step by step correction control means.

2. A device as claimed in claim 1, wherein the treatment head is provided with a separate end piece which is attached to the exterior surface of the short cylindrical portion of the treatment head, said end piece including a support disc on which are distributed a plurality of said laser diodes.

3. A device as claimed in claim 2, wherein the plurality of laser diodes comprises three laser diodes mounted to form the apices of a triangle.

* * * * *